United States Patent
Pujol Onofre et al.

(10) Patent No.: US 11,382,889 B2
(45) Date of Patent: Jul. 12, 2022

(54) NRF2 ACTIVATORS FOR THE PREVENTION AND/OR TREATMENT OF AXONAL DEGENERATION

(71) Applicants: INSTITUT D'INVESTIGACIÓ BIOMÈDICA DE BELLVITGE (IDIBELL), Barcelona (ES); INSTITUCIÓ CATALANA DE RECERCA I ESTUDIS AVANÇATS, Barcelona (ES)

(72) Inventors: Aurora Pujol Onofre, Barcelona (ES); Stéphane Fourcade, Barcelona (ES)

(73) Assignees: INSTITUT D'INVESTIGACIÓ BIOMÈDICA DE BELLVITGE (IDIBELL), L'Hospitalet de Llobregat (ES); INSTITUCIÓ CATALANA DE RECERCA I ESTUDIS AVANÇATS, Barcelona (ES)

(*) Notice: Subject to any disclaimer, the term of this patent is extended or adjusted under 35 U.S.C. 154(b) by 0 days.

(21) Appl. No.: 15/957,601

(22) Filed: Apr. 19, 2018

(65) Prior Publication Data

US 2019/0321322 A1    Oct. 24, 2019

(51) Int. Cl.
*A61K 31/225* (2006.01)
*A61P 25/00* (2006.01)
*A61K 9/00* (2006.01)

(52) U.S. Cl.
CPC .......... *A61K 31/225* (2013.01); *A61K 9/0053* (2013.01); *A61P 25/00* (2018.01)

(58) Field of Classification Search
CPC .................................................. A61K 31/225
See application file for complete search history.

(56) References Cited

U.S. PATENT DOCUMENTS

| 8,507,476 | B2* | 8/2013 | Fayol | A61P 25/24 |
| | | | | 514/221 |
| 8,865,747 | B2* | 10/2014 | Pujol Onofre | A61K 31/4439 |
| | | | | 514/342 |
| 2013/0287732 | A1* | 10/2013 | Goelz | A61K 38/215 |
| | | | | 424/85.6 |
| 2015/0132747 | A1* | 5/2015 | Lukashev | G01N 33/5023 |
| | | | | 435/6.1 |

FOREIGN PATENT DOCUMENTS

WO    WO 2015/100511 A1    12/2014

OTHER PUBLICATIONS

Pitarokoili et al., Dimethyl Fumarate Ameliorates Lewis Rat Expeimental Autoimmune Neuritis and Mediates Axonal Protection, 2015, PLoS ONE, 10(11): e0143416, pp. 1-17 (Year: 2015).*
Morato et al., Pioglitazone halts axonal degeneration in a mouse model of X-linked adrenoleukodystrophy, 2013, Brain, 136, pp. 2432-2443 (Year: 2013).*
Fourcade, S., et al., Oxidative Stress, Mitochondrial and Proteostasis Malfunction in Adrenoleukodystrophy: A Paradigm for Axonal Degeneration, Free Radical Biology and Medicine 88:18-29, 2015.
Guide for the Care and Use of Laboratory Animals, Eighth Edition, The National Academies Press, Washington, D.C., 2011, 246 pages.
Rattay et al., "Nerve ultrasound characterizes AMN polyneuropathy as inhomogeneous and focal hypertrophic", Orphanet Journal of Rare Diseases, vol. 13, Article No. 194, Nov. 3, 2018.

* cited by examiner

*Primary Examiner* — Rei Tsang Shiao
(74) *Attorney, Agent, or Firm* — Knobbe Martens Olson & Bear, LLP

(57) ABSTRACT

Therapeutic solutions for axonal degeneration include use of NRF2 activators in prevention and/or treatment of axonal degeneration. A method of prevention and/or treating axonal degeneration includes administering a therapeutically effective amount of a NRF2 activator selected from a GSK3 inhibitor or the compound of formula (I):

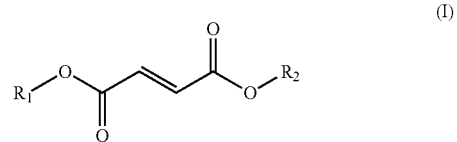

(I)

wherein $R_1$ and $R_2$, which may be the same or different, independently represent H, a linear, branched wherein $R_1$ and $R_2$, which may be the same or different, independently represent a linear, branched or cyclic, saturated or unsaturated $C_{1-6}$ alkyl radical, a pharmaceutical salt thereof or a metabolite or precursor of the dimethyl fumarate to a patient in need of the treatment.

11 Claims, 4 Drawing Sheets

NRF2 ACTIVATORS FOR THE PREVENTION AND/OR TREATMENT OF AXONAL DEGENERATION

BACKGROUND OF THE INVENTION

Field of the Invention

The present invention relates to therapeutic solutions for axonal degeneration. More particularly the invention is related to the use of NRF2 activators in the prevention and/or treatment of axonal degeneration.

Description of the Related Art

The transcription factor NRF2-nuclear factor (erythroid-derived 2)-like 2 is the master regulator of endogenous antioxidant response, regulating a battery of genes that coordinate a protective response against oxidative stress.

Oxidative stress and mitochondrial dysfunction have been demonstrated to participate in the onset and/or progression of neurodegeneration in age-related neurodegenerative diseases such as Parkinson's disease (PD), Huntington's disease (HD), Alzheimer's disease (AD) and amyotrophic lateral sclerosis (ALS), and many forms of hereditary spastic paraplegia (SPG or HSP).

A common theme among these diseases, as well as in the prototypic demyelinating disease multiple sclerosis (MS), is axonal degeneration. The rare neurometabolic disorder X-linked adrenoleukodystrophy (X-ALD) is a paradigm for axonal degeneration of similar molecular bases (Fourcade, Ferrer, Pujol) Free Radic Biol Med. 2015 November; 88(Pt A):18-29.

Axonal degeneration, which occurs at early stages of neurodegenerative disorders (ND), also takes place as a consequence of normal aging. Compelling evidence indicate that the degeneration of axons precedes clinical symptoms in NDs and occurs before cell body loss, constituting an early event in the pathological process and providing a potential therapeutic target to treat neurodegeneration before neuronal cell death.

The process of axonal degeneration consists in the destruction of axons.

Notably, increasing evidence in recent years has raised the awareness of axonal pathology as an early, common contributor to the pathomechanism of different age-related neurological diseases. This pathological overlapping shared by NDs represents an important focus of research not only for the impact in our current understanding of the etiology of this diseases, but also for the drug development field as it might provide potential targets for future therapeutic and, most importantly, preventative strategies aimed at limiting axonal and therefore neuronal degeneration in NDs.

The patent application WO2015100511 describes the treatment of axonal degeneration with necrostatin-1.

Although several treatments have already been described, there is still a need of new treatment to prevent/or treat the axonal degeneration.

SUMMARY OF THE INVENTION

The inventors have found a method of prevention and/or treating axonal degeneration, said method comprising administering a therapeutically effective amount of a NRF2 activator selected from: a GSK3 inhibitor or the compound of formula (I)

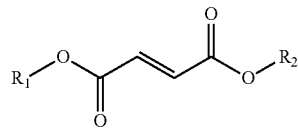

wherein $R_1$ and $R_2$, which may be the same or different, independently represent a linear, branched wherein $R_1$ and $R_2$, which may be the same or different, independently represent a H, linear, branched or cyclic, saturated or unsaturated $C_{1-6}$ alkyl radical, a pharmaceutical salt thereof or a metabolite or precursor of the dimethyl fumarate to a patient in need of said treatment.

It is provided that any GSK3 inhibitor that is currently known or which can be discovered can be used with the presently disclosed subject matter.

As used herein, "preventing" means causing the clinical symptoms of the disease state not to develop i.e., inhibiting the onset of disease, in a subject that may be exposed to or predisposed to the disease state, but does not yet experience or display symptoms of the disease state.

As used herein, the term "treatment", or "treating" refers to any method used to partially or completely alleviate, ameliorate, relieve, inhibit, delay onset of, reduce severity of and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response. In some embodiments, a therapeutically effective amount of a substance is an amount that is sufficient, when administered to a subject suffering from or susceptible to a disease, disorder, and/or condition, to treat, prevent, and/or delay and/or alleviate one or more symptoms of the disease. Furthermore, an effective amount may be administered via a single dose or via multiple doses within a treatment regimen.

As used herein, the term "patient" refers to any organism to which a composition of this invention may be administered. Typical subjects include animals (e.g., mammals such as mice, rats, rabbits, non-human primates, and humans).

As used herein, "a metabolite or precursor of the dimethyl fumarate" refers to a derivative dimethyl fumarate present in the metabolism of it and include any useful metabolite or precursor.

b) NRF2-dependent antioxidative genes (Hmox1, Nqo1 and Gst α 3) expression in WT (n=8), Abcd1⁻ (n=8) and Abcd1⁻+DMF (n=8) mice spinal cord at 12 months of age. Gene expression levels were normalized relative to Rplp0. Quantification is represented as fold change to WT mice.

c) Mitochondrial DNA (mtDNA) levels in WT (n=8), Abcd1⁻ (n=8) and Abcd1⁻+DMF (n=8) mice spinal cord at 12 months of age. mtDNA content was measured by quantitative RT-PCR and expressed as the ratio of mtDNA (CytB levels) to nuclear DNA (nDNA, Cebpa levels). Quantification is depicted as fold change to WT mice.

d) Sirt1, Pgc-1α, Nrf1 and Tfam expression was measured by quantitative RT-PCR in WT (n=8), Abcd1⁻ (n=8) and Abcd1⁻+DMF (n=8) mice spinal cord at 12 months of age. Gene expression levels were normalized relative to Rplp0. Quantification is depicted as fold change to WT mice.

e) ATP levels in WT (n=8), Abcd1⁻ (n=8) and Abcd1⁻+DMF (n=8) mice spinal cord at 12 months of age. Quantification is represented as fold change to WT mice. Data are shown as mean±SD (*$p<0.05$, $p<0.01$, *$p<0.001$ after one-way ANOVA test followed by Tukey's post-hoc test; #$p<0.05$ after one-way ANOVA test followed by Dunnett's post-hoc test; $p<0.05$, $p<0.01$ after non-parametric Kruskal-Wallis' test).

Figure 2:
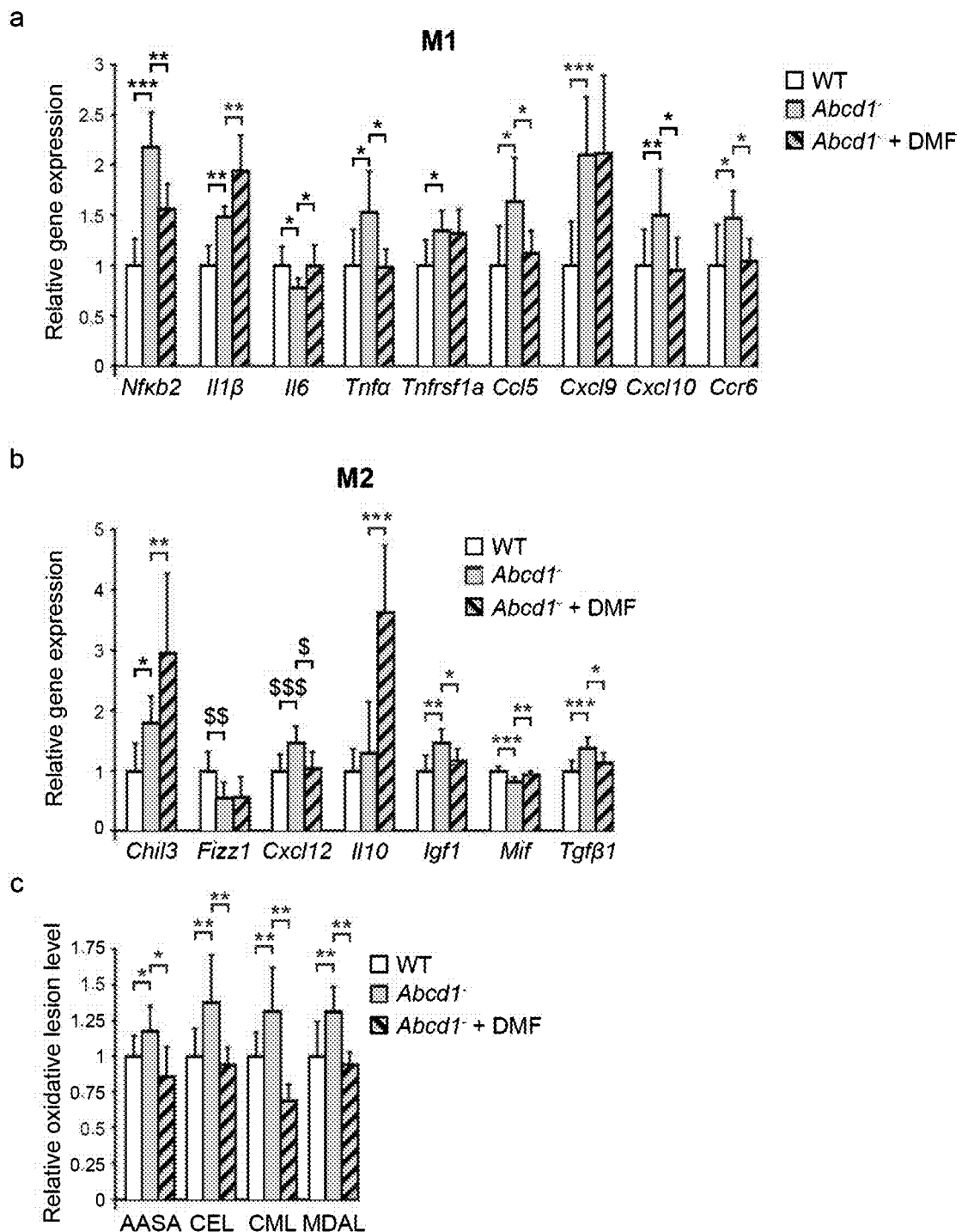

FIG. 2 shows that the DMF treatment prevents inflammatory imbalance and oxidative damage to proteins and lipids in Abcd1⁻ mice.

a) Th1 (Nfκb2, Il1β, Il6, Tnfα, Tnfrsf1a, Ccl5, Cxcl9, Cxcl10, Ccr6) and b) Th2 (Fizz1, Chil3, Cxcl12, Il10, Igf1, Mif, Tgfβ1) inflammatory profile in WT (n=8), Abcd1⁻ (n=8) and Abcd1⁻+DMF (n=8) mice spinal cord at 12 months of age. Cytokines, chemokines and other inflammation-related genes expression was measured by quantitative RT-PCR. Gene expression levels were normalized relative to Rplp0. Quantification is depicted as fold change to WT mice. c) Oxidative lesions to lipids and proteins in WT (n=5), Abcd1⁻ (n=5) and Abcd1⁻+DMF (n=5) mice spinal cord at 12 months of age. AASA, CEL, CML and MDAL levels were measured by GC/MS. Quantification is represented as fold change to WT mice. Data are shown as mean±SD (*$p<0.05$, $p<0.01$, *$p<0.001$ after one-way ANOVA test followed by Tukey's post-hoc test; $p<0.05$, $p<0.01$, $p<0.001$ after non-parametric Kruskal-Wallis' test).

Figure 3:
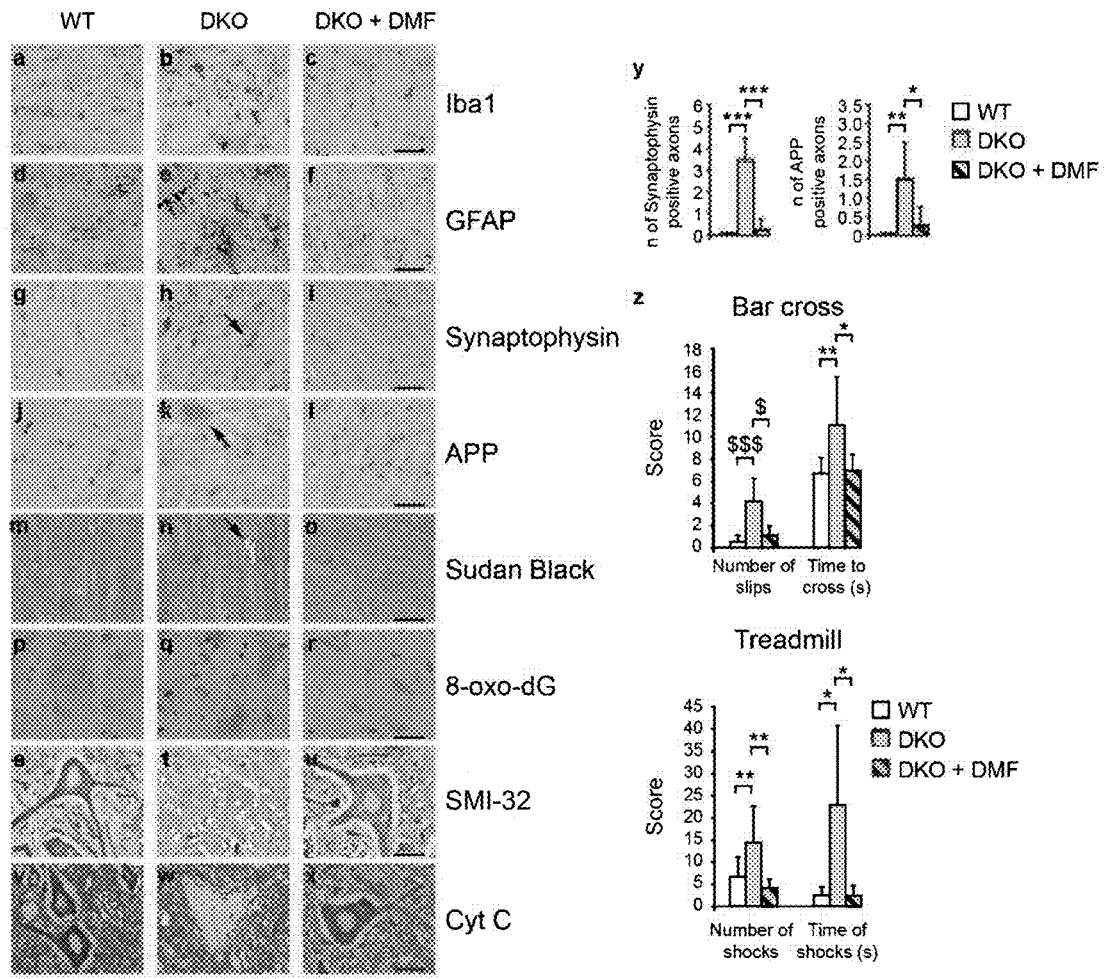

FIG. 3 shows that the DMF treatment prevents axonal degeneration and locomotor impairment in Abcd1⁻/Abcd2⁻/⁻ mice.

a-x) Immunohistological analysis of axonal pathologies performed in 18-month-old WT, Abcd1⁻/Abcd2⁻/⁻ (DKO) and Abcd1⁻/Abcd2⁻/⁻ mice treated with DMF (DKO+DMF) (n=5 per genotype and condition). Spinal cord immunohistological sections were processed for (a-c) Iba1, (d-f) GFAP, (g-i) Synaptophysin, (j-l) APP, (m-o) Sudan black, (p-r) 8-oxo-dG, (s-u) CYT C and (v-x) SMI-32 immunostaining. Representative images for (a, d, g, j, m, p, s, v) WT, (b, e, h, k, n, q, t, w) DKO, and (c, f, i, l, o, r, u, x) DKO+DMF are shown. Scale bars=25 μm (a-r) and 125 μM (s-x). y) Quantification of synaptophysin and APP accumulations in spinal cord immunohistological sections of WT (n=5), DKO (n=5) and DKO+DMF (n=5) mice. z) Bar-cross and treadmill tests performed on 18-month-old WT (n=14), Abcd1⁻// Abcd2⁻/⁻ (DKO) (n=16) and Abcd1⁻//Abcd2⁻/⁻ mice treated with DMF (DKO+DMF) (n=14). Data showed refers to number of slips and time (seconds) spent to cross the bar, in the bar cross. In the treadmill test, data showed refers to number of shocks and time of shocks at the last time point measured (7 minutes and 30 seconds). Values are expressed as mean±SD (*$p<0.05$, $p<0.01$, *$p<0.001$ after one-way ANOVA test followed by Tukey's post hoc test; $p<0.05$, $p<0.001$ after non-parametric Kruskal-Wallis' test).

Figure 4:
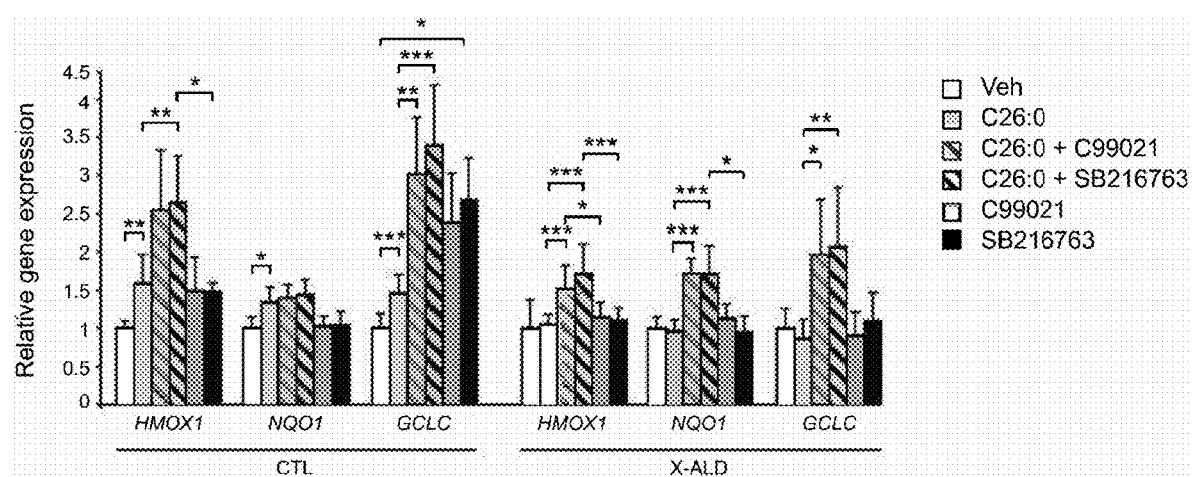

FIG. 4 shows that the GSK3 activators restore a normal NRF2 response in X-ALD fibroblasts.

DETAILED DESCRIPTION OF THE PREFERRED EMBODIMENT

As mentioned above, an aspect of the present invention relates to a method of prevention and/or treating axonal degeneration, said method comprising administering a therapeutically effective amount of a NRF2 activator selected from: a GSK3 inhibitor or the compound of formula (I)

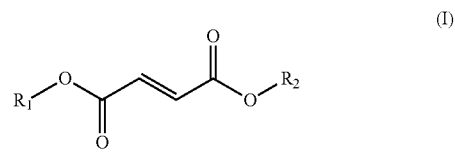

wherein $R_1$ and $R_2$, which may be the same or different, independently represent a linear, branched wherein $R_1$ and $R_2$, which may be the same or different, independently represent H, a linear, branched or cyclic, saturated or unsaturated $C_{1-6}$ alkyl radical, a pharmaceutical salt thereof or a metabolite or precursor of the dimethyl fumarate to a patient in need of said treatment.

In a preferred embodiment the NRF2 activator is a GSK3 inhibitor. In a preferred embodiment the GSK3 inhibitor is selected from: (6-[[2-[[4-(2,4-dichlorophenyl)-5-(5-methyl-1H-imidazol-2-yl)-pyrimidinyl]amino]-3-pyridinecarbonitrile or (3-(2,4-dichlorophenyl)-4-(1-methyl-1H-indol-3-yl)-1H-pyrrole-2,5-dione.

The inventors have found that the fumaric acid derivatives are useful for the treatment of X-ALD.

X-linked adrenoleukodystrophy (X-ALD) is caused by mutations in the Abcd1 gene that encodes the peroxisomal membrane protein ALDP which is involved in the transmembrane transport of very long-chain fatty acids (VLCFA; ≥C22). A defect in ALPD results in elevated levels of VLCFA in plasma and tissues.

The main forms of the disease are: 1) cerebral childhood ALD or ccALD (approximately 40% of cases), affecting boys between 5-10 years, which is associated with a strong inflammatory reaction in the central nervous system white matter and may involve autoimmune mechanisms; and 2) adrenomyeloneuropathy or AMN (60%), which affects adult males between 20-50 years of age and heterozygous women after the age of 40, and where the spinal cord and peripheral nerves are affected.

X-ALD is characterized by oxidative stress, misfolded protein aggregates, myelin and axonal degeneration and neuroinflammation.

The inventors have found that the administration of DMF (dialkyl fumarates) in the mouse models of X-ALD normalized molecular defects as: mitochondrial depletion, bioenergetic failure, oxidative damage and inflammation, and most importantly halted axonal degeneration and locomotive disability.

In a preferred embodiment in the method of prevention and/or treating axonal degeneration the NRF2 activator is the compound of formula (I)

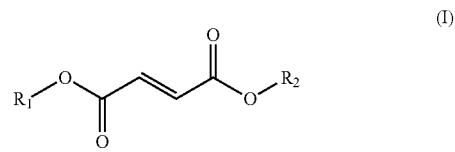

wherein $R_1$ and $R_2$, which may be the same or different, independently represent a linear, branched wherein $R_1$ and $R_2$, which may be the same or different, independently represent a H, linear, branched or cyclic, saturated or unsaturated $C_{1-6}$ alkyl radical, a pharmaceutical salt thereof, or a metabolite or precursor of the dimethyl fumarate, and the patient is a X-ALD patient In a preferred embodiment the X-linked adrenoleukodystrophy (X-ALD) is selected from the group consisting of adult adrenomyeloneuropathy (AMN) or cerebral childhood ALD. In a particular embodiment, the adrenoleukodystrophy is adrenomyeloneuropahy (AMN).

The $C_{1-6}$ alkyl radicals, for example: methyl, ethyl, n-propyl, isopropyl, n-butyl, sec-butyl, t-butyl, pentyl, hexyl. Preferably at least one of the radicals $R_1$ or $R_2$ is methyl or ethyl. Especially preferred are the dimethyl fumarate, methyl ethyl fumarate and diethyl fumarate. Most preferred is dimethyl fumarate.

In a preferred embodiment the present invention relates to a method of preventing and/or treating X-ALD, said method comprising administering a therapeutically effective amount of a NRF2 activator as defined above, and a compound selected from: pioglitazone, fingolimod, siponimod, temsirolimus and tauroursodeoxycholic acid (TUDCA) to a patient in need of said prevention and/or treatment. Preferred the compound is selected from: pioglitazone, fingolimod, siponimod, and tauroursodeoxycholic acid (TUDCA).

In a most preferred embodiment the present invention relates to a method of preventing and/or treating X-ALD, wherein the NRF2 activator is the compound of formula (I)

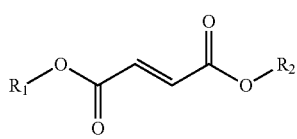

wherein $R_1$ and $R_2$, which may be the same or different, independently represent H, a linear, branched wherein $R_1$ and $R_2$, which may be the same or different, independently represent a linear, branched or cyclic, saturated or unsaturated $C_{1-6}$ alkyl radical, a pharmaceutical salt thereof or a metabolite or precursor of the dimethyl fumarate and a compound selected from: pioglitazone, fingolimod, siponimod, temsirolimus and tauroursodeoxycholic acid (TUDCA) to a patient in need of said prevention and/or treatment.

The invention can occur at any pharmaceutical form of administration considered appropriate for the selected administration route, for example systemic, oral, parenteral or topical administration. Especially preferably is oral administration.

The therapeutically effective amount of the compound of the invention or pharmaceutically acceptable salt thereof or the metabolite or precursor of the dimethyl fumarate, can vary within a wide range and in general will vary depending on the particular circumstances of application, duration of the exposure and other considerations. When the patient is a human the therapeutically effective amount is in a range between 7 mg/kg/day and 9 mg/kg/day.

EXAMPLES

The following examples are provided for illustrative means, and are not meant to be limiting of the present invention.

Example 1

Mouse Experiments

We used male mice of a pure C57BL/6J background. All methods employed in this study were in accordance with the Guide for the Care and Use of Laboratory Animals (Guide, 8th edition, 2011, NIH) and European (2010/63/UE) and Spanish (RD 53/2013) legislation. Experimental protocol had been approved by IDIBELL, IACUC (Institutional Animal Care and Use Committee) and regional authority (3546 DMAH, Generalitat de Catalunya, Spain). IDIBELL animal facility has been accredited by The Association for Assessment and Accreditation of Laboratory Animal Care (AAALAC, Unit 1155). Animals were housed at 22° C. on specific-pathogen free conditions, in a 12-hour light/dark cycle, and ad libitum access to food and water. Cages contained 3 to 5 animals.

We used two X-ALD mouse models in this study. We characterized the biochemical signs of adult X-ALD in $Abcd1^-$ mice at 12 months of age. These mice show biochemical signs of pathology, including oxidative stress and energetic homeostasis impairment, before the first clinical signs of AMN-like pathology (axonopathy and locomotor impairment) appear at 20 months.

To address the therapeutic effect of DMF, we assessed the clinical signs of AMN in $Abcd1^-/Abcd2^{-/-}$ (DKO) mice, which display increased VLCFA accumulation in the spinal cord, higher levels of oxidative damage to proteins, and a more severe AMN-like pathology with an earlier onset at 12 months of age.

For biochemical analysis, we killed the mice and stored the tissues at −80° C. after snap-freezing them in liquid nitrogen. For histological analysis, spinal cord was harvested from 18-month-old mice after perfusing them with 4% paraformaldehyde (PFA; Sigma-Aldrich, Ref. 441244) in 0.1 M phosphate buffer pH 7.4. Histological and behavioural tests were performed in a blind way with respect to the animal's genotype and for the treatment administered.

DMF Administration to Mice

DMF was mixed into AIN-76A chow from Dyets (Bethlehem, Pa., USA) to provide a dose of 100 mg/kg/day. Human equivalent dose would be 8 mg/kg/day (240 mg in a typical 60 kg person). This is equivalent to the starting dose of BG-12/Tecfidera that is 120 mg twice a day for MS patients (EMA/204830/2013).

For the characterization of biochemical signs on adult X-ALD mice, 8-months-old animals were randomly assigned to one of the following dietary groups for 4 months. Group I: wild-type (WT) mice received normal AIN-76A chow (n=12); group II: $Abcd1^-$ mice received normal AIN-76A chow (n=12); group III: $Abcd1^-$ mice received AIN-76A chow containing DMF (n=12). To evaluate the effect of DMF on the clinical signs of AMN-like pathology, 12-months-old animals were randomly assigned to one of the following dietary groups for 6 months. Group I: WT mice received normal AIN-76A chow (n=14); group II: $Abcd1^-/Abcd2^{-/-}$ mice received normal AIN-76A chow (n=16); group III: $Abcd1^-/Abcd2^{-/-}$ mice received AIN-76A chow containing DMF (n=14). DMF had no effect on weight or food intake under any treatment protocol, and none of the mice administered with DMF experienced any adverse events or death during treatment.

NRF2 Activation by DMF Prevents Mitochondrial Depletion and Bioenergetic Failure in X-ALD Mice In order to verify that the dietary administration of DMF was effective, we first measured NRF2 protein levels and mRNA expression of three classical NRF2-target genes (Hmox1, Nqo1 and Gstα3). Interestingly, DMF induced both NRF2 protein levels (FIG. 1a) and NRF2 target genes expression in Abcd1⁻ mice spinal cord at 12 months of age (FIG. 1b).

Next, we examined the effect of DMF on mitochondrial dysfunction in Abcd1⁻ mouse spinal cord at 12 months of age. DMF normalized mitochondrial DNA (mtDNA) levels (FIG. 1c) and mitochondrial biogenesis genes mRNA expression (sirtuin-1, Sirt1; peroxisome proliferator-activated receptor gamma coactivator 1-alpha, Pgc-1 α; nuclear respiratory factor-1, Nrf1; and transcription factor A, mitochondrial, Tfam) (FIG. 1d).

Figure 1:
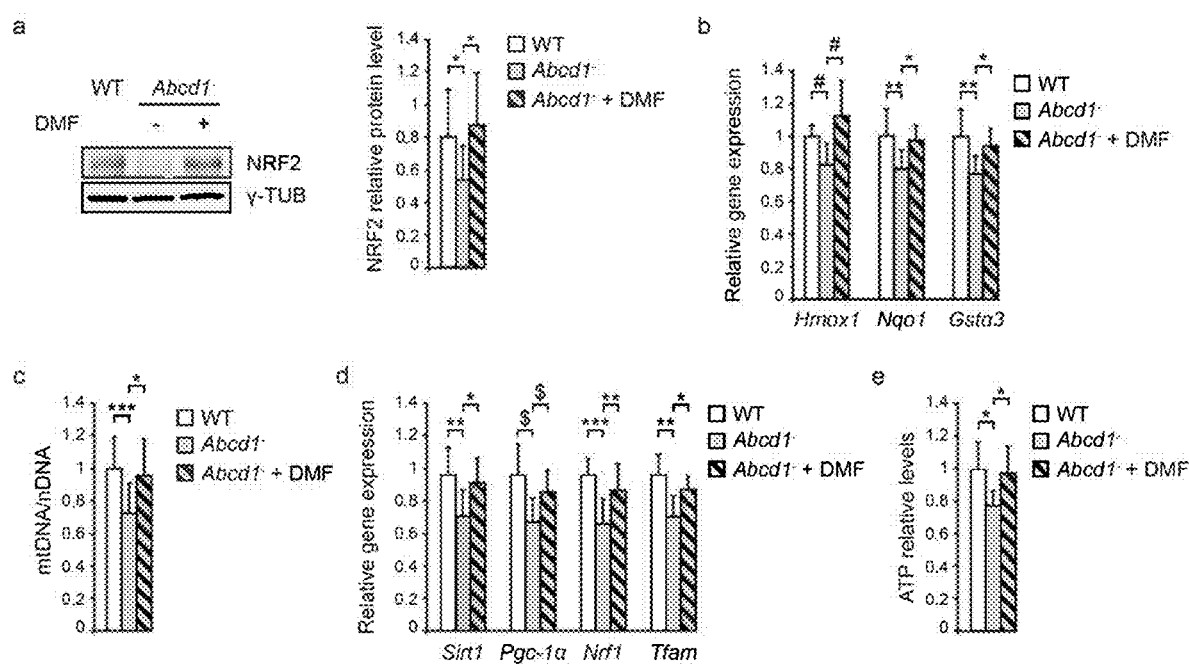
FIG. 1 shows the NRF2 activation by DMF prevents mitochondrial depletion and bioenergetic failure in Abcd1⁻ mice a) NRF2 protein levels in WT (n=6), Abcd1⁻ (n=6) and DMF-treated Abcd1⁻ mice (Abcd1⁻+DMF, n=6) mice spinal cord at 12 months of age. Protein levels were normalized relative to γ-TUB and quantification is depicted as fold change to WT (Wild type) mice.

We revealed that DMF prevented bioenergetic failure in X-ALD mouse spinal cord at 12 months of age, as ATP levels were normalized by DMF treatment (FIG. 1e). In summary, DMF activated NRF2-dependent antioxidant pathway, as well as prevented mitochondrial depletion and bioenergetic failure in Abcd1⁻ mice spinal cord. DMF treatment prevents inflammatory imbalance and oxidative damage to proteins and lipids in X-ALD mice.

Although AMN patients do not present overt brain inflammation leading to demyelination, we have found a low-grade inflammatory dysregulation in Abcd1⁻ mouse spinal cord and in AMN patients. In Abcd1⁻ mouse, a functional genomics assay detected NFκB-mediated inflammatory pathway activation in Abcd1⁻ mouse spinal cord, and increased expression of several proinflammatory genes. Regarding AMN patients, we have recently described a general dysregulation of inflammatory pathways in peripheral blood mononuclear cells (PBMCs) and plasma from AMN patients. As DMF is a classical immunomodulatory drug, we examined its effects on mRNA expression of several inflammation-related genes in Abcd1⁻ mice spinal cord.

At 12 months of age, Abcd1⁻ mouse exhibited a general imbalance of both M1 and M2 markers in spinal cord. Nuclear factor kappa B subunit 2 (Nfκb2), which belongs to the non-canonical NFκB pathway, as well as the majority of M1 markers were increased in Abcd1⁻ mouse spinal cord, including interleukin 1 beta (Il1β), tumour necrosis factor alpha (Tnfα), tumour necrosis factor receptor superfamily member 1a (Tnfrsf1a), chemokine (C-C motif) ligand 5 (Ccl5), chemokine (C-X-C motif) ligand 9 (Cxcl9), chemokine (C-X-C motif) ligand 10 (Cxcl10) and chemokine (C-C motif) receptor type 6 (Ccr6) (FIG. 2a). Also, some M2 markers were upregulated, as, chitinase-like 3 (Chil3), chemokine (C-X-C motif) ligand 12 (Cxcl12), insulin-like growth factor 1 (Igf1) and transforming growth factor, beta 1 (Tgfβ1) (FIG. 2b). Only few of them were decreased in Abcd1⁻ mouse spinal cord: interleukin 6 (Il6), resistin like alpha (Retnla, also called Fizz1) and macrophage migration inhibitory factor (Mif) (FIG. 2a-b).

DMF prevented most of the alterations observed in this inflammatory profile, normalizing mRNA levels of Nfκb2, Il6, Tnfα, Ccl5, Cxcl10, Ccr6 (FIG. 2a), and Mif, Cxcl12, Tgfβ1, Igf1 (FIG. 2b). However, DMF had no effect on Tnfrsf1a, Cxcl9 and Fizz1 mRNA (FIG. 2a-b). Furthermore, DMF exacerbated the induction of Il1β and Chil3 mRNA in Abcd1⁻ mouse spinal cord (FIG. 2a-b). Interestingly, interleukin 10 (Il10) mRNA, an anti-inflammatory cytokine, was upregulated by DMF (FIG. 2b).

DMF Prevents Axonal Degeneration in X-ALD Mice

To evaluate the effect of DMF on axonal degeneration and locomotor impairment in X-ALD, Abcd1⁻/Abcd2⁻/⁻ mice (DKO) were fed with chow including DMF (100 mg/kg).

First, we assessed immunohistochemical signs of neuropathology, present in DKO mice, at 18 months of age, and characterized by (i) microgliosis; (ii) astrocytosis; (iii) axonal degeneration, shown by accumulation of amyloid precursor protein (APP) and synaptophysin in axonal swellings; (iv) lipidic myelin debris, showed by Sudan Black staining (v) oxidative damage to DNA, indicated by increased 8-oxo-7,8-dihydro-2'-deoxyguanosine (8-oxo-dG) staining; (vi) decreased mitochondrial content observed by cytochrome c (Cyt C) staining in motor neurons; and (vii) unhealthy motor neurons seen by reduced staining of SMI-32, an antibody that labels a non-phosphorylated epitope of neurofilament proteins (FIG. 3 a-y).

DMF reversed microgliosis and astrocytosis in DKO mice spinal cord (FIG. 3 a-f), prevented the accumulation of APP and synaptophysin in axons (FIG. 3 g-l, y), halted the appearance of myelin debris along the spinal cord (FIG. 3 m-o), and reduced oxidative damage to DNA shown by a reduced 8-oxo-dG staining in DKO mice treated with DMF (FIG. 3 p-r). In addition, mitochondrial levels and motor neurons health were improved with DMF treatment (FIG. 3 s-x).

Altogether, these data revealed that DMF treatment ameliorated X-ALD neuropathology in Abcd1⁻/Abcd2⁻/⁻ mice.

DMF Reverses Locomotive Deficits of X-ALD Mice

Next, we measured the effect of DMF on the neurological phenotype of DKO mice at 18 months of age, by performing bar cross and treadmill tests at the end of the treatment.

As already described, DKO mice took longer time to cross the bar, and tended to slip off more times while crossing the bar. After DMF treatment, treated DKO mice behaved similar to WT mice, indicating that DMF ameliorated the ability of DKO mice to cross the bar (FIG. 3z).

DKO behaved worse than WT in the treadmill test. The total number and duration of shocks was higher than in WT. DMF treatment also improved the performance of DKO mice in this test, up to the level of WT mice (FIG. 3z).

Oral administration of dimethyl fumarate, in the mouse models of X-ALD (Abcd1⁻ and Abcd1⁻/Abcd2⁻/⁻) normalized molecular defects as i) mitochondrial depletion, ii) bioenergetic failure, iii) oxidative damage and iv) inflammation, and most importantly halted axonal degeneration and locomotor disability. In summary, these data indicate that DMF treatment was able to halt the progression of locomotor deficits in Abcd1⁻/Abcd2⁻/⁻ mice.

Example 2

Patient's fibroblasts treated with two different GSK-3B inhibitors, CT99021 and SB216763, restore a normal NRF2 response in X-ALD fibroblasts. This means that the NRF-2 target genes HMOX1, NQO1 and GCLC increase their expression when incubated with excess VLCFA. See FIG. 4 (n=8 per genotype and condition). Gene expression normalized relative to RPLP0. Quantification depicted as fold change to vehicle-treated (Veh) fibroblasts.

In conclusion, activation of the NRF-2 pathway with either GSK3B inhibitors or with Dimethylfumarate, are valuable therapeutic approaches for adrenoleukodystrophy or other axonopathies.

What is claimed is:

1. A method of treating X-linked adrenoleukodystrophy (X-ALD) in a patient in need thereof, said method comprising administering to the patient a therapeutically effective amount of a NRF2 activator selected from the group consisting of a GSK3 inhibitor and the compound of formula (I):

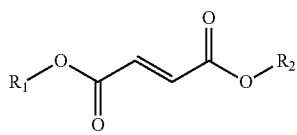

(I)

wherein $R_1$ and $R_2$, which may be the same or different, independently represent H, a linear, branched wherein $R_1$ and $R_2$, which may be the same or different, independently represent a linear, branched or cyclic, saturated or unsaturated $C_{1-6}$ alkyl radical, a pharmaceutical salt thereof or a metabolite or precursor of dimethyl fumarate, wherein the GSK3 inhibitor is selected from the group consisting of (6-[[2-[[4-(2,4-dichlorophenyl)-5-(5-methyl-1H-imidazol-2-yl)-pyrimidinyl]amino]-3-pyridinecarbonitrile or (3-(2,4-dichlorophenyl)-4-(1-methyl-1H-indol-3-yl)-1Hpyrrole-2,5-dione.

2. The method according to claim 1, wherein the NRF2 activator is the GSK3 inhibitor.

3. The method according to claim 1, wherein the NRF2 activator is the compound of formula (I).

4. The method according to claim 3, wherein the X-ALD is adrenomyeloneuropahy (AMN) or cerebral childhood ALD.

5. The method according to claim 1, wherein the compound of formula (I) is selected from the group consisting of dimethyl fumarate, methyl ethyl fumarate and diethyl fumarate.

6. The method according to claim 5, wherein the compound of formula (I) is dimethyl fumarate.

7. The method according to claim 1, wherein the compound of formula (I) or the pharmaceutical salt thereof is administered orally.

8. The method according to claim 1, wherein the patient is a human.

9. The method according to claim 1, said method further comprising administering a compound selected from the group consisting of pioglitazone, fingolimod, siponimod, temsirolimus and tauroursodeoxycholic acid (TUDCA) to the X-ALD patient.

10. The method of preventing and/or treating X-ALD according to claim 9, wherein the NRF2 activator is the compound of formula (I).

11. The method according to claim 1, wherein the method consists of said administering.

* * * * *